United States Patent [19]

Le Roy et al.

[11] Patent Number: 4,554,350
[45] Date of Patent: Nov. 19, 1985

[54] 3-(1-HALO-2-OXOETHYL)CEPHALOSPORIN INTERMEDIATES

[75] Inventors: Pierre Le Roy; Daniel Farge, both of Thiais; Claude Moutonnier, Le Plessis Robinson; Jean-Francois Peyronel, Palaiseau; Bernard Plau, Creteil, all of France

[73] Assignee: Rhone-Poulenc Sante, Courbevoie, France

[21] Appl. No.: 522,261

[22] Filed: Aug. 11, 1983

[30] Foreign Application Priority Data

Aug. 13, 1982 [FR] France .................................. 82 14093

[51] Int. Cl.$^4$ ........................................... C07D 501/24
[52] U.S. Cl. ....................................... 544/22; 544/24; 544/25; 544/28
[58] Field of Search ........................................... 544/22

[56] References Cited

U.S. PATENT DOCUMENTS 4,415,735  11/1983  Farge et al. ............................ 544/22

OTHER PUBLICATIONS

Organic Chemistry by Hendrickson et al, p. 208.
Advanced Organic Chemistry, by J. March, pp. 86, 89, 105, and 113.

Primary Examiner—Donald G. Daus
Assistant Examiner—Robert Benson
Attorney, Agent, or Firm—Stevens, Davis, Miller & Mosher

[57] ABSTRACT

New cephalosporin derivatives of the formula:

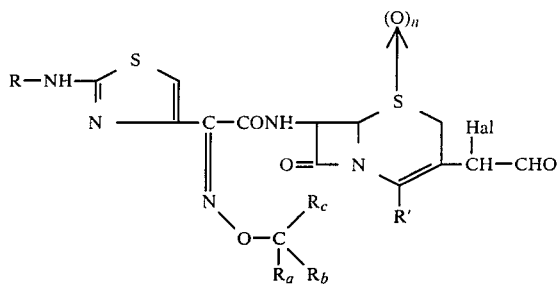

in which R is an amino-protecting radical, R' is a protected carboxyl radical, Hal is a halogen atom, $R_a$, $R_b$ and $R_c$ are hydrogen atoms, or $R_a$ is a protected carboxyl radical and $R_b$ and $R_c$, which are identical or different, are hydrogen atoms, or $C_1$-$C_4$ alkyl radicals, or together form a $C_2$-$C_5$ alkylene radical, and n=0 or 1, their isomeric forms and mixtures thereof, are useful for the preparation of cephalosporins which have antibacterial properties.

6 Claims, No Drawings

3-(1-HALO-2-OXOETHYL)CEPHALOSPORIN INTERMEDIATES

The present invention relates to new cephalosporin derivatives and processes for their preparation.

Belgian Pat. No. 883,418 and European Patent Application No. 53,962 have described cephalosporins carrying a formylmethyl substituent in the 3-position.

The present invention provides the new cephalosporin derivatives of the formula:

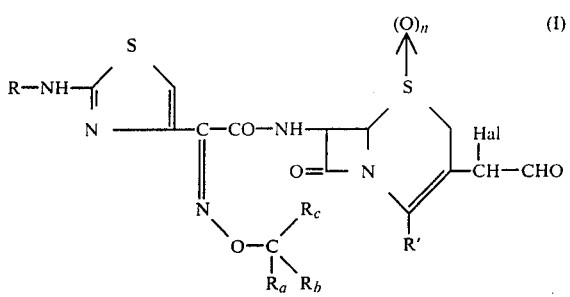

in which R represents an amino-protecting radical, R' represents a protected carboxyl radical, Hal represents a halogen atom (e.g. chlorine, bromine or iodine), and either $R_a$, $R_b$ and $R_c$ each represent a hydrogen atom, or $R_a$ represents a protected carboxyl radical and $R_b$ and $R_c$, which are identical or different, represent hydrogen atoms or alkyl radicals containing 1 to 4 carbon atoms, or together form an alkylene radical containing 2 to 5 carbon atoms, and n is equal to 0 or 1, and the isomeric forms of the said cephalosporin derivatives and mixtures thereof. It is to be understood that alkyl radicals referred to in this specification are linear or branched and, unless otherwise specified, contain 1 to 4 carbon atoms.

It is to be understood that, in the general formula (I) (and in the general formulae used hereafter), the group $—OCR_aR_bR_c$ is in the syn position.

Furthermore, the compounds of the general formula (I), which all contain a radical —CH(Hal)—CHO— in the 3-position, have isomeric forms; it is to be understood that the epimers and mixtures thereof fall within the scope of the present invention.

Furthermore, if the symbols $R_b$ and $R_c$ in the general formula (I) are different, diastereoisomers exist; it is to be understood that these isomeric forms and mixtures thereof fall within the scope of the present invention.

The amino-protecting radical R should be easily removable and can be chosen e.g. from t-butoxycarbonyl, 2,2,2-trichloroethoxycarbonyl, trityl, benzyl, benzyloxycarbonyl, formyl, trifluoroacetyl, p-nitrobenzyloxycarbonyl, p-methoxybenzyloxycarbonyl or diphenylphosphinoyl groups or a radical defined by the general formula:

in which Z is alkyl of 1 to 4 carbon atoms, or 2,2,2-trichloroethyl, or phenyl or benzyl, these last two being unsubstituted or substituted by halogen, alkyl, alkoxy or nitro, or the symbols Z together form an alkylene radical containing 2 or 3 carbon atoms, it being possible for the above phosphorus-containing radicals to be introduced by applying the method described by A. MORIMOTO et al., J. Chem. Soc. Perkin I, 1109 (1980).

The acid-protecting radical contained in R' or $R_a$ is a radical which can easily be removed without affecting the rest of the molecule. By way of example, R' or $R_a$ can be protected by a t-butyl, 2,2,2-trichloroethyl, benzhydryl, p-nitrobenzyl or p-methoxybenzyl radical.

According to the invention, the cephalosporin derivatives of the general formula (I) in which n equals 0 can be prepared by reacting a halogenating agent with an enamine of the general formula:

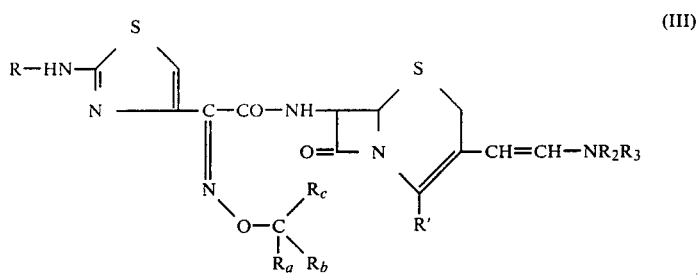

[in which R, R', $R_a$, $R_b$ and $R_c$ are as defined above for the general formula (I) and $R_2$ and $R_3$, which are identical or different, represent alkyl radicals (unsubstituted or substituted by alkoxy or dialkylamino) or phenyl radicals, or form, together with the nitrogen atom to which they are attached, a 5-membered or 6-membered heterocyclic ring which may contain another heteroatom chosen from nitrogen, oxygen or sulphur and unsubstituted or substituted by alkyl] and then hydrolysing the product formed.

By way of example, an enamine of the general formula (III) in which $R_2$ and $R_3$ are each a methyl radical is used.

The following may be mentioned amongst the halogenating agents: halogens, N-halogenoamides [e.g. N-bromosuccinimide (or N-chlorosuccinimide), N-bromoacetamide (or N-chloroacetamide) or dibromohydantoin] and alkyl hypohalites (e.g. ethyl or t-butyl hypochlorite or t-butyl hypobromite).

The halogenation is generally carried out in an organic solvent such as an ether (e.g. tetrahydrofuran or dioxane), a chlorinated solvent (e.g. methylene chloride or chloroform), an ester (e.g. ethyl acetate), an alcohol (e.g. methanol or ethanol), an amide (e.g. dimethylformamide or dimethylacetamide), a nitrile (e.g. acetonitrile) or a ketone (e.g. acetone), or in a mixture of such solvents, at a temperature of between −70° and 0° C.

The hydrolysis is carried out at a temperature of between −70° and 20° C.

According to the invention, the products of the general formula (I) in which n=1 can be obtained by oxidising a product of the general formula (I) in which n=0 by any method which does not affect the rest of the molecule.

The reaction is carried out, in particular, under the conditions described in German Application No. 2,637,176, in particular in the presence of m-chloroperbenzoic acid in an organic solvent such as methylene chloride.

The enamines of the general formula (III) can be prepared in accordance with the method described in Belgian Pat. No. 883,416 or in European Patent Application No. 53,961.

The cephalosporin derivatives according to the invention are useful for the preparation of 3-thiazolyl-cephalosporins of the general formula:

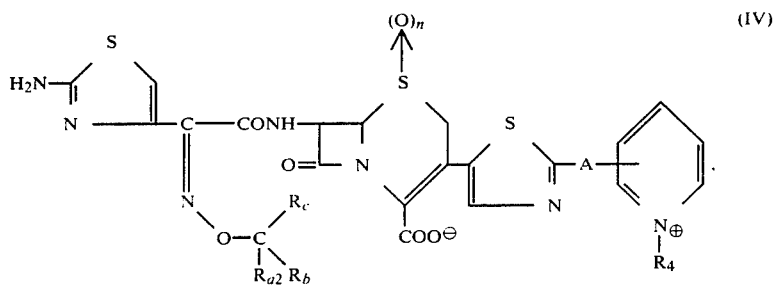

(IV)

in which $R_b$, $R_c$ and n are defined as above, the symbol $R_{a2}$ is a hydrogen atom or represents a carboxyl radical, the symbol A represents a single bond or a divalent radical chosen from amongst —$CH_2$—, —NH— or —NHCO—, attached to the 3-position or 4-position of the pyridinio radical, and the symbol $R_4$ represents a methyl, carboxymethyl, carbamoylmethyl, benzyl or allyl radical.

It is understood that the products of the general formula (IV) exist either in the form of internal salts (one of the carboxyl groups present in the molecule being in the form of a carboxylato radical) or in the form of an acid solvate of this betaine.

The products of the general formula (IV) can be obtained from the products of the general formula (I) by the following procedure:

A product of the general formula:

$$R_5CSNH_2 \quad (V),$$

in which $R_5$ is an amino radical or a radical of the structure:

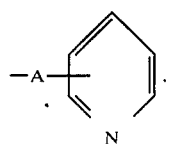

in which A is defined as above, is reacted with a cephalosporin derivative of the general formula (I) and then, if appropriate, with a dehydrating agent, and the sulphoxide obtained is reduced, if appropriate, and the protecting radicals are removed, if appropriate, to give a cephalosporin derivative of the general formula:

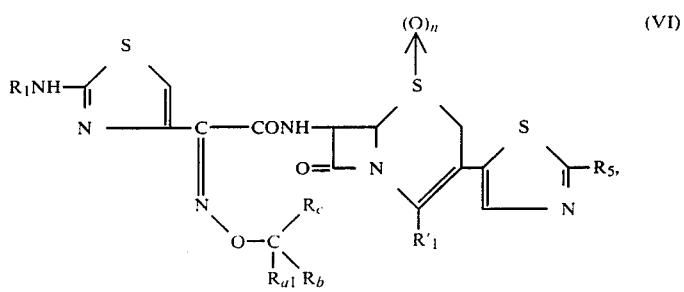

(VI)

in which $R_b$, $R_c$, $R_5$ and n are defined as above, $R'_1$ is a free or protected carboxyl radical, $R_1$ is a hydrogen atom or an amino-protecting radical and $R_{a1}$ is a hydrogen atom or a free or protected carboxyl radical.

The reaction is generally carried out in an organic or aqueous-organic medium, e.g. in solvents (or mixtures of solvents) such as alcohols (methanol and ethanol), ethers (tetrahydrofuran and dioxane), ketones (acetone), nitriles (acetonitrile), secondary amides (dimethylformamide and dimethylacetamide), esters (ethyl acetate) or acids (acetic acid and formic acid), in the presence or absence of a base (sodium hydroxide, potassium hydroxide, alkali metal carbonates or bicarbonates, alkali metal salts of carboxylic acids or tertiary amines), at a temperature of between −50° C. and the reflux temperature of the reaction mixture.

It is sometimes preferable to introduce a dehydrating agent.

The following may be mentioned amongst the dehydrating agents which can be used: sulphonyl halides [e.g. tosyl chloride, methanesulphonyl chloride or a halide of the type $R°SO_2Cl$ in which $R°$ is alkyl, trifluoromethyl (or trichloromethyl) or phenyl optionally substituted by halogen, methyl or nitro], phosphoryl halides (e.g. phosphorus oxychloride) or sulphonyl chloride, either in a basic solvent [pyridine or an amide (e.g. dimethylformamide, dimethylacetamide or hexamethylphosphorotriamide)] or in a chlorinated solvent (e.g. chloroform or methylene chloride), an ether (e.g. tetrahydrofuran), an ester, a ketone, a nitrile or an aromatic solvent, in the presence of a tertiary amine (e.g. pyridine, quinoline or triethylamine).

If appropriate, the sulphoxide is reduced in accordance with the methods described in German Application No. 2,637,176.

The acid-protecting groups can be removed e.g.:

in the case of a t-butyl, p-methoxybenzyl or benzhydryl group: by treatment in an acid medium, under the conditions described below for the removal of the amino-protecting trityl radical. In the case of the benzhydryl radical, the reaction can be carried out in the presence of anisole or by treatment with aluminium chloride under the conditions described by T. Tsuji et. al., Tet. Lett., 30, 2793 (1979); or in the case of a 2,2,2-trichloroethyl or p-nitrobenzyl group: by reduction (in particular by treatment with zinc in acetic acid or, in the case of the p-nitrobenzyl group, by hydrogenolysis).

The amine-protecting groups can be removed e.g.:

in the case of a t-butoxycarbonyl, trityl, p-methoxybenzyloxycarbonyl or formyl radical: by treatment in an acid medium. Preferably, trifluoroacetic acid is used, the reaction being carried out at a temperature of between 0° and 20° C., or alternatively anhydrous or aqueous formic, phosphoric or polyphosphoric acid is used at a temperature of between 20° and 60° C., or alternatively para-toluenesulphonic or methanesulphonic acid is used in acetone or acetonitrile, at a temperature of between 20° C. and the reflux temperature of the reaction mixture. Under these conditions, the product of the general formula (VI) can be obtained in the form of the trifluoroacetate, the solvate with formic acid, the phosphate, the methanesulphonate or the para-toluenesulphonate, from which the amine group can be freed by any method which is in itself known for obtaining an amine from one of its salts without affecting the rest of the molecule. The reaction is carried out, in particular, by bringing the product into contact with an ion exchange resin or by reacting it with an organic base;

in the case of 2,2,2-trichloroethoxycarbonyl or p-nitrobenzyloxycarbonyl radical or a radical of the general formula (II) in which Z is 2,2,2-trichloroethyl or nitrobenzyl: by reduction (in particular by treatment with zinc in acetic acid);

in the case of a benzyl or benzyloxycarbonyl radical: by catalytic hydrogenation;

in the case of a trifluoroacetyl radical: by treatment in a basic medium;

in the case of a radical of the general formula (II): in accordance with the method described in Belgian Pat. No. 833,619; or in the case of a diphenylphosphinoyl radical: in accordance with the method described by P. HAAKE et al., J. Am. Chem. Soc. 95, 8073 (1973).

Then, 1° if $R_5$ is a radical of the structure:

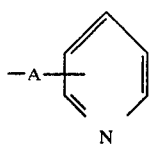

a halide or a sulphonate of the general formula:

$$R_4-X \quad \text{(VII)},$$

in which $R_4$ is defined as above or represents a protected carboxymethyl radical and X represents a halogen atom chosen from amongst iodine, bromine or chlorine, an alkylsulphonyloxy radical [in which the alkyl part, which contains 1 to 4 carbon atoms, can be substituted by one or more halogen atoms] or a phenylsulphonyloxy radical [in which the phenyl radical can be substituted by one or more substituents chosen from amongst halogen atoms or alkyl or nitro radicals], is reacted with a cephalosporin derivative of the general formula (VI) and then the sulphoxide obtained is reduced, if appropriate, and the protecting radicals represented by R or contained in $R_{a1}$ or $R'_1$ are removed.

The reaction is generally carried out in an organic solvent such as an amide (dimethylformamide, hexamethylphosphorotriamide or dimethylacetamide), a nitrile (e.g. acetonitrile), a ketone (e.g. acetone) or a nitro derivative (e.g. nitromethane or nitrobenzene), or in a mixture of such solvents, at a temperature of between 0° and 80° C.

If appropriate, the sulphoxide is reduced in accordance with the methods described in German Patent Application No. 2,637,176.

The protecting radicals are removed under the conditions described above.

Alternatively, 2° if $R_5$ is an amino radical and if it is desired to obtain a product of the general formula (IV) in which the symbol A is a divalent radical —NHCO—, the product of the general formula (VI) obtained, in which $R_1$ is an amino-protecting radical and $R_5$ is an amino radical, is converted by any known method for forming an amide group without affecting the rest of the molecule.

The reaction is generally carried out using a nicotinic or isonicotinic acid derivative in which the nitrogen atom is quaternised by a radical $R_4$ such as defined above, it being understood that if $R_4$ is a carboxymethyl radical, the carboxyl radical is protected.

The reaction is advantageously carried out using an acid halide, and the sulphoxide obtained is then reduced, if appropriate, and the protecting radicals are removed.

If the nicotinic or isonicotinic acid derivative is used in its acid form, the condensation is carried out with the 3-(2-aminothiazol-5yl)-cephalosporin of the general formula (VI) in which $R_1$ is a protecting radical, in the presence of a condensation agent such as a carbodiimide (e.g. dicyclohexylcarbodiimide), N,N'-carbonyldiimidazole or 2-ethoxy-1-ethoxycarbonyl-1,2-dihydroquinoline, at a temperature of between −20° and 40° C., and the protecting groups are then removed.

If the acid halide (which can be prepared in situ) is used, the condensation is carried out in an inert organic solvent such as an ether (e.g. tetrahydrofuran or dioxane), a chlorinated solvent (e.g. chloroform or methylene chloride), an amide (e.g. dimethylformamide or dimethylacetamide) or a ketone (e.g. acetone), or in mixtures of the above solvents, in the presence of an acid acceptor such as an epoxide (e.g. propylene oxide) or such as an organic nitrogen base [e.g. pyridine, dimethylaminopyridine, N-methylmorpholine or a trialkylamine (e.g. triethylamine)], or in the presence of a silylating agent such as bis-trimethylsilylacetamide, or alternatively in an aqueous-organic medium in the presence of an alkaline condensation agent such as sodium bicarbonate, and the reaction is carried out at a temperature of between −40° and 40° C.; the protecting groups are then removed under the conditions described above.

The products of the general formula (V) can be prepared by reacting ammonia gas with the corresponding isothiocyanate or with a corresponding alkyl or aryl dithiocarbamate, or by reacting hydrogen sulphide with the corresponding nitrile, and in particular if $R_5$ represents nicotinoylamino or isonicotinoylamino, in accordance with the method of W. H. PIKE, Chem. Ber., 6, 755 (1873).

The new products according to the present invention and the products of the general formula (IV) can be purified, if appropriate, by physical methods such as crystallisation, chromatography or ultrafiltration.

The cephalosporin derivatives of the general formula (IV) and their pharmaceutically acceptable salts are particularly valuable antibacterial agents with a broad spectrum. They show a remarkable activity in vitro and in vivo against Gram-positive and Gram-negative germs.

In virto, the products of the general formula (IV) have been shown to be active at a concentration of between 1 and 30 μg/cc against staphylococcus strains sensitive to penicillin G (*Staphylococcus aureus* Smith) and at a concentration of between 0.01 and 1 μg/cc against *Escherichia coli*, NIHJ strain. Furthermore, the products of the general formula (IV) in which $R_a$ is a carboxyl radical have been shown to be active at a concentration of between 2 and 15 μg/cc against *Pseudomonas aeruginosa*.

In vivo, the products of the general formula (IV) have been shown to be active at a dose of between 0.5 and 15 mg/kg per day, administered subcutaneously, against experimental infections caused in mice by *Staphylococcus aureus* Smith (sensitive to penicillin G).

Furthermore, the products of the general formula (IV) have been shown to be non-toxic to mice at a dose of 1 mg/kg, administered subcutaneously.

Amongst the products of the general formula (I), those which are more especially valuable are the products in which the symbol R is a trityl radical, the symbol R' is a benzhydryloxycarbonyl radical, the symbol Hal is a bromine atom and the symbols $R_a$, $R_b$ and $R_c$ each represent a hydrogen atom, or alternatively $R_a$ represents a t-butoxycarbonyl radical and Rb and Rc represent alkyl radicals, and also their isomeric forms and mixtures thereof.

The examples which follow, which are given without implying a limitation, illustrate the present invention.

EXAMPLE 1

A solution of bromine (0.1 cc) in methylene chloride (2 cc) is added in the course of 5 minutes to a solution of the E form of the syn isomer of 2-benzhydryloxycarbonyl-3-(2-dimethylaminovinyl)-7-[2-methoxyimino-2-(2-tritylaminothiazol-4-yl)-acetamido]-8-oxo-5-thia-1-azabicyclo[4.2.0]oct-2-ene (1.72 g) in dry tetrahydrofuran (30 cc), cooled to −60° C. The reaction mixture is stirred for 90 minutes at the same temperature and then poured into a mixture of ethyl acetate (150 cc) and distilled water (150 cc); the organic phase is washed with distilled water (2×100 cc) and then with a saturated solution of sodium chloride (100 cc), dried over sodium sulphate and concentrated to dryness under reduced pressure (4 kPa) at 30° C. to give the syn isomer of 2-benzhydryloxycarbonyl-3-(1-bromo-2-oxoethyl)-7-[2-methoxyimino-2-(2-tritylaminothiazol-4-yl)-acetamido]-8-oxo-5-thia-1-azabicyclo[4.2.0]oct-2-ene (mixture of the two diastereoisomers in respect of the substituent in the 3-position) (1.75 g).

Proton NMR spectrum (350 MHz, CDCl₃, δ in ppm, J in Hz): mixture of two diastereoisomers in 50/50 proportions: 3.35, 3.54, 3.66 and 3.75 (4d, J=17.5, 2H, —S—CH₂— of the two diastereoisomers); 4.08 (s, 3H, =N—OCH₃); 5.10 and 5.16 (2d, J=5, 1H, —H in the 6-position of the two diastereoisomers); 6 and 6.03 (2s, 1H, >CHBr of the two diastereoisomers); 5.95 to 6.10 (mt, 1H, —H in the 7-position of the two diastereoisomers); 6.76 (s, 1H, —H of the thiazole); 6.91 and 6.98 (2s, 1H, —COO—CH(C₆H₅)₂ of the two diastereoisomers); 6.80 to 7.10 (mt, 2H, —CONH— and —NH—C(C₆H₅)₃ of the two diastereoisomers); 7.20 to 7.60 (mt, aromatic protons); 9.30 and 9.32

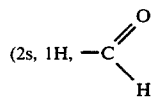

(2s, 1H, of the two diastereoisomers).

EXAMPLE 2

A solution of the E form of the syn isomer of 2-benzhydryloxycarbonyl-7-[2-(2-t-butoxycarbonyl-prop-2-yl-oxyimino)-2-(2-tritylaminothiazol-4-yl)-acetamido]-3-(2-dimethylaminovinyl)-8-oxo-5-thia-1-azabicyclo[4.2.0]oct-2-ene (0.6 g) in tetrahydrofuran (10 cc) is cooled to −60° C. A solution of bromine (0.034 cc) in methylene chloride (1 cc) is added. After stirring for 20 minutes at −60° C., the reactin mixture is poured into a mixture of ethyl acetate (25 cc) and distilled water (50 cc). The organic phase is washed with distilled water (3×20 cc), dried and concentrated to dryness under reduced pressure (4 kPa) at 30° C. to give the syn isomer of 2-benzhydryloxycarbonyl-3-(1-bromo-2-oxo-ethyl)-7-[2-(2-t-butoxycarbonylprop-2-yl-oxyimino)-2-(2-tritylaminothiazol-4-yl)-acetamido]-8-oxo-5-thia-1-azabicyclo[4.2.0]oct-2-ene (mixture of the two diastereoisomers in respect of the substituent in the 3-position) (0.64 g) in the form of a hard beige foam.

Proton NMR spectrum (350 MHz, CDCl₃, δ in ppm, J in Hz) (characteristic signals of the two diastereoisomers A and B): 1.45 (s, 9H, —C(CH₃)₃ of A and B); 1.55 to 1.7 (4s, 4×3H, —C(CH₃)₂— of A and B); 5.10 and 5.15 (2d, J=4, 2H, H₆ of A and B); 6.0 and 6.02 (2s, 2H, >CHBr of A and B); 6.73 (s broad, 2H, H of the thiazole of A and B); 6.83 and 6.94 (2s, 2H, —CO₂CHAr₂ of A and B); 9.28 and 9.3 (2s, 2H, —CHO of A and B).

REFERENCE EXAMPLE 1

Thionicotinamide (0.28 g) and pyridine (0.16 g) are added to a solution of the syn isomer of 2-benzhydryloxycarbonyl-3-(1-bromo-2-oxoethyl)-7-[2-methoxyimino-2-(2-tritylaminothiazol-4-yl)-acetamido]-8-oxo-5-thia-1-azabicyclo[4.2.0]oct-2-ene (mixture of the two diastereoisomers) (1.66 g) in tetrahydrofuran (20 cc) and the mixture is heated at 50° C. for 90 minutes. The reaction mixture is subsequently cooled to 0° C. and then treated successively with methanesulphonyl chloride (0.23 g) and triethylamine (0.56 cc). After 30 minutes at 0° C., the reaction mixture is poured into a mixture of a saturated solution of sodium bicarbonate (200 cc) and ethyl acetate (100 cc); the organic phase is decanted, washed with distilled water (150 cc) and with a saturated solution of sodium chloride (150 cc) and then dried over magnesium sulphate. The residue obtained after evaporation of the solvent to dryness under reduced pressure (4 kPa) at 40° C. is chromatographed on a column (height: 30 cm, diameter: 1.5 cm) containing silica gel (0.04–0.06 mm), elution being carried out under a pressure of 0.5 bar (50 kPa) with a mixture of cyclohexane and ethyl acetate (30/70 by volume) and 50 cc fractions being collected. Fractions 18 to 26 are combined and concentrated to dryness under reduced pressure (30 mm Hg; 4 kPa) at 30° C. to give the syn isomer of 2-benzhydryloxycarbonyl-7-[2-methoxyimino-2-(2-tritylaminothiazol-4-yl)-acetamido]-8-oxo-3-[2-(pyridin-3-yl)-thiazol-5-yl]-5-thia-1-azabicyclo[4.2.0]oct-2-ene (0.18 g) in the form of a beige powder.

Proton NMR spectrum (250 MHz, CDCl₃, δ in ppm, J in Hz): 3.60 and 3.76 (2d, J=17.5, 2H, —SCH₂—); 4.11 (s, 3H, =NOCH₃); 5.18 (d, J=4, 1H, H in the 6-position); 6.04 (dd, J=4 and 9, 1H, H in the 7-position); 6.75 (s, 1H, H in the 5-position of the thiazole); 6.96 (s, 1H, —CO₂CHAr₂); 7.0 to 7.4 (b, 27H, aromatic protons + —CON$\overline{\text{H}}$— + H in the 5-position of the pyridine); 7.57 (s, 1H, H in the 4-position of the thiazole); 8.04 (dd, 1H, H in the 4-position of the pyridine); 8.67 (dd, 1H, H in the 6-position of the pyridine); 8.94 (d, 1H, H in the 2-position of the pyridine).

The syn isomer of 2-benzhydryloxycarbonyl-7[2-methoxyimino-2-(2-tritylaminothiazol-4-yl)-acetamido]-8-oxo-3-[2-(pyridin-3-yl)-thiazol-5-yl]-5-thia-1-azabicyclo[4.2.0]oct-2-ene (1.1 g) is treated with formic acid (20 cc) containing anisole (2 cc) for 30 minutes at 50° C. and the reaction mixture is then concentrated to dryness under reduced pressure (1 mm Hg; 0.13 kPa) at 40° C. The residue is taken up in ethanol (20 cc), which is evaporated off under reduced pressure (30 mm Hg; 4 kPa) at 40° C.; this operation is repeated a further 2 times. The residue is solidified with ethanol (150 cc). The solid is filtered off, washed with ethanol (2×5 cc) and ethyl ether (3×20 cc) and dried to give the syn isomer of 7-[2-(2-aminothiazol-4-yl)-2-methoxyiminoacetamido]-2-carboxy-8-oxo-3-[2-(pyridin-3-yl)-thiazol-5-yl]-5-thia-1-azabicyclo[4.2.0]oct-2-ene (0.56 g) in the form of a pale yellow solid.

Infra-red spectrum (KBr, characteristic bands (Cm⁻¹): 3380–3320, 3200, 3100, 2200, 1780, 1680, 1620, 1530, 1040, 865, 810, 710.

Proton NMR spectrum (250 MHz, DMSO-d₆, δ in ppm, J in Hz): 3.87 (s, 3H, =NOCH₃); 3.88 and 4.0 (2d, J=17, 2H, —SCH₂—); 5.28 (d, J=5, 1H, H in the 6-position); 5.9 (dd, J=5 and 8, 1H, H in the 7-position); 6.77 (s, 1H, H in the 5-position of the thiazole); 7.22 (s, 2H, —NH₂); 7.55 (dd, J=8 and 5, 1H, H in the 5-position of the pyridine); 8.02 (s, 1H, H in the 4-position of the thiazole); 8.28 (m, 1H, H in the 4-position of the pyridine); 8.68 (dd, J=5 and 1.5, 1H, H in the 6-position of the pyridine); 9.11 (d, J=1.5, 1H, H in the 2-position of the pyridine); 14.5 to 12 (b broadened, 1H, —COO$\overline{\text{H}}$).

A mixture of the syn isomer of 7-[2-(2-aminothiazol-4-yl)-2-methoxyiminoacetamido]-2-carboxy-8-oxo-3-[2-(pyridin-3-yl)-thiazol-5-yl]-5-thia-1-aza-bicyclo[4.2.0]oct-2-ene (0.06 g) with methyl iodide (0.04 cc) is stirred at 25° C. for 24 hours in N,N-dimethylformamide (0.5 cc). The reaction mixture is diluted with ethyl acetate (10 cc); a solid precipitates and is filtered off, washed with ethyl acetate (2×2 cc) and then with ethyl ether (2×5 cc) and dried under reduced pressure (0.1 mm Hg; 0.013 kPa) at 25° C. to give crude syn isomer of 7-[2-aminothiazol-4-yl)-2-methoxyiminoacetamide]-2-carboxylato-3-[2-(1-methyl-3-pyridinio)-thiazol-5-yl]-8-oxo-5-thia-1-azabicyclo[4.2.0]oct-2-ene hydroiodide (0.06 g) in the form of a yellow solid.

Proton NMR spectrum (250 MHz, DMSO-d₆, δ in ppm, J in Hz): 3.91 (s, 3H, =NOCH₃); 3.99 (s, broad, 2H, —SCH₂—); 4.46 (s, 3H,

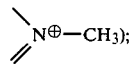

5.31 (d, J=5, 1H, H in the 6-position); 5.99 (dd, J=5 and 9, 1H, H in the 7-position); 6.89 (s, 1H, H in the 4-position of the thiazole); 8.25 (s, 1H, H in the 5-position of the thiazole); 8.27 (b, 1H, H in the 5-position of the pyridinio); 9.05 (d, 1H, H in the 4-position of the pyridinio); 9.14 (b, 1H, H in the 6-position of the pyridinio); 9.69 (s, 1H, H in the 2-position of the pyridinio); 9.86 (d, J=9, 1H, —CONH—).

Crude syn isomer of 7-([2-(2-aminothiazol-4-yl)-2-methoxyiminoacetamido]-2-carboxylato-3-[2-(1-methyl-3-pyridinio)-thiazol-5-yl]-8-oxo-5-thia-1-azabicyclo-[4.2.0]oct-2-ene hydroiodide (7.6 g), obtained under conditions identical to those described above, is taken up in distilled water (500 cc) and ethyl acetate (250 cc); after filtration and decantation of the aqueous phase, the latter is washed with ethyl acetate (150 cc) and treated with basic IR 45 resin until a pH of 4.7 is reached. The resin is removed by filtration and the aqueous solution is lyophilised. The lyophilisate is solidified with distilled water (50 cc) to give the syn isomer of 7-[2-(2-aminothiazol-4-yl)-2-methoxyiminoacetamido]-2-carboxylato-3-[2-(1-methyl-3-pyridinio)-thiazol-5-yl]-8-oxo-5-thia-1-azabicyclo[4.2.0]oct-2-ene (3.15 g) in the form of an orange powder.

Infra-red spectrum (KBr, characteristic bands in cm⁻¹): 3600–2500, 1765, 1670, 1610, 1530, 1380, 1030, 770, 675.

Proton NMR spectrum (250 MHz, DMSO-d₆, δ in ppm, J in Hz): 3.71 and 3.84 (2d, J=17, 2H, —S—CH₂—); 3.86 (s, 3H, =N—OCH₃);

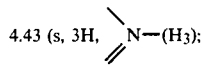

4.43 (s, 3H, 5.15 (d, J=5, 1H, —H in the 6-position); 5.65 (dd, J=8 and 5, 1H, —H in the 7-position); 6.76 (s, 1H, —H in the 5-position of the thiazole); 7.27 (b, 2H, —NH₂); 8.08 (s, 1H, —H in the 4-position of the thiazole); 8.14 (dd, J=8 and 6, 1H, —H in the 5-position of the pyridinio); 8.83 (d, J=8, 1H, —H in the 4-position of the pyridinio); 8.98 (d, J=6, 1H, —H in the 6-position of the pyridinio); 9.48 (s, 1H, —H in the 2-position of the pyridinio); 9.64 (d, J=8, 1H, —CONH—).

REFERENCE EXAMPLE 2

A mixture of (pyridin-3-yl)-thiourea (0.08 g) and the syn isomer of 2-benzhydryloxycarbonyl-3-(1-bromo-2-oxoethyl)-7-[2-(2-t-butoxycarbonylprop-2-yl-oxyimino)-2-(2-tritylaminothiazol-4-yl)-acetamido]-8-oxo-5-thia-1-azabicyclo[4.2.0]oct-2-ene (mixture of the two diastereoisomers in respect of the substituent in the 3-position) (0.55 g) in tetrahydrofuran (10 cc) is stirred for 35 minutes at 25° C. and then treated with pyridine (0.042 cc) and water (1 cc). The reaction mixture is stirred for 16 hours at 25° C. and then poured into a mixture of ethyl acetate (50 cc) and 0.2 N hydrochloric acid (50 cc). The organic solution is washed with a saturated solution of sodium bicarbonate (50 cc), water (3×50 cc) and then with a saturated solution of sodium chloride (20 cc) and dried over magnesium sulphate. The residue obtained after evaporation of the solvent to dryness under reduced pressure (4 kPa) at 30° C. is chromatographed on a column (height: 24 cm, diameter: 2 cm) containing silica gel (0.04-0.06 mm), elution being carried out under a pressure of 0.5 bar (50 kPa) with a mixture of cyclohexane and ethyl acetate (15/85 by volume) and 15 cc fractions being collected. Fractions 7 to 13 are combined and concentrated to dryness under reduced pressure (4 kPa) at 30° C. to give the syn isomer of 2-benzhydryloxycarbonyl-7-[2-(2-t-butoxycarbonylprop-2-yl-oxyimino)-2-(2-tritylaminothiazol-4-yl)-acetamido]-8-oxo-3-[2-(pyridin-3-yl-amino)-thiazol-5-yl]-5-thia-1-azabicyclo[4.2.0]oct-2-ene (0.39 g) in the form of a hard yellow foam.

Infra-red spectrum (CHBr$_3$), characteristic bands (cm$^{-1}$): 3400, 1790, 1725, 1680, 1525, 1495, 1450, 1370, 750, 740.

Proton NMR spectrum (250 MHz, DMSO-d$_6$, δ in ppm, J in Hz): 1.37 (s, 9H, —C(CH$_3$)$_3$); 1.43 (s, 6H, >C(CH$_3$)$_2$); 3.77 and 3.89 (2d, J=17.5, 2H, —S—CH$_2$—); 5.28 (d, J=5, 1H, —H in the 6-position); 5.83 (dd, J=8 and 5, 1H, —H in the 7-position); 6.72 (s, 1H, —H in the 5-position of the thiazole); 6.89 (s, 1H, —COO—CH(C$_6$H$_5$)$_2$); 7 to 7.4 (mt, aromatic protons, —H in the 4-position of the thiazole and —H in the 5-position of the pyridine); 8.07 (d broad, J=7.5, 1H, —H in the 4-position of the pyridine); 8.19 (d broad, J=5, 1H, —H in the 6-position of the pyridine); 8.68 (d, J=2, 1H, —H in the 2-position of the pyridine); 8.83 (s, 1H, —NH—C(C$_6$H$_5$)$_3$); 9.48 (d, J=8, 1H, —CO—NH—); 10.44 (s, 1H, >N—H).

A solution of m-chloroperbenzoic acid (2.59 g) in methylene chloride (52 cc) is run, over a period of 30 minutes, into a solution, cooled to 0° C., of the syn isomer of 2-benzhydryloxycarbonyl-7-{2-[(2-t-butoxycarbonylprop-2-yl)-oxyimino]-2-(2-tritylaminothiazol-4-yl)-acetamido}-8-oxo-3-[2-(pyridin-3-yl-amino)-thiazol-5-yl]-5-thia-1-azabicyclo[4.2.0]oct-2-ene (13.46 g) in methylene chloride (123 cc). The mixture is stirred for 15 minutes at 0° C. and the reaction solution is then diluted with methylene chloride (200 cc). The mixture is washed successively with a semi-saturated solution of sodium bicarbonate (200 cc) and distilled water (2×200 cc). The organic phase is then dried over anhydrous magnesium sulphate and filtered and the filtrate is then concentrated under reduced pressure (100 mm Hg; 13.3 kPa) at 30° C. The residue is purified by chromatography on a column (height=29 cm, diameter=5.8 cm) containing silica gel (0.04-0.06 mm), elution being carried out under a pressure of 0.4 bar with a mixture of cyclohexane and ethyl acetate (10/90 by volume) (2 liters) and 125 cc fractions being collected. Fractions 11 to 15 are combined and concentrated to dryness under reduced pressure (30 mm Hg; 4 kPa) at 30° C. to give the syr isomer of 2-benzhydryloxycarbonyl-7-{2-[(2-t-butoxycarbonyl-prop-2-yl)-oxyimino]-2-(2-tritylaminothiazol-4-yl)-acetamido}-8-oxo-3-[2-(pyridin-3-yl-amino)-thiazol-5-yl]-5-thia-1-azabicyclo[4.2.0]oct-2-ene 5-oxide (0.70 g) in the form of a hard yellow foam.

Infra-red spectrum (CHBr$_3$), characteristic bands (cm$^{-1}$): 3390, 1800, 1725, 1680, 1530, 1495, 1450, 1370, 1050, 700.

Proton NMR spectrum (250 MHz, CDCl$_3$, δ in ppm, J in Hz): 1.41 (s, 9H, —C(CH$_3$)$_3$); 1.56 and 1.58 (2s, 6H, >C(CH$_3$)$_2$); 3.25 and 3.84 (2d, J=18.5, 2H, —S—CH$_2$—); 4.56 (d, J=5, 1H, —H in the 6-position); 6.19 (dd, J=9.5 and 5, 1H, —H in the 7-position); 6.72 (s, 1H, —H in the 5-position of the thiazole); 6.92 (s, 1H, —COO—CH—(C$_6$H$_5$)$_2$); 7.01 (s, 1H, —H in the 4-position of the thiazole); 7.11 (dd, J=5 and 7.5, —H in the 5-position of the pyridine); 7.05 to 7.45 (mt, aromatic protons); 7.9 (ddd, J=7.5, 2 and 1.5, 1H, —H in the 4-position of the pyridien); 8.0 (d, j=9.5, 1H, —CONH—); 8.21 (dd, J=5 and 1.5, 1H, —H in the 6-position of the pyridine); 8.6 (d, J=2, 1H, —H in the 2-position of the pyridine); 8.73 (b, 1H, —NHC(C$_6$H$_5$)$_3$).

A solution of the syn isomer of 2-benzhydroyloxycarbonyl-7-{2-[(2-t-butoxycarbonyl-prop-2-yl)-oxyimino]-2-(2-tritylaminothiazol-4-yl)-acetamido}-8-oxo-3-[2-(pyridin-3-yl-amino)-thiazol-5-yl]-5-thia-1-azabicyclo[4.2.0]oct-2-ene 5-oxide (1.67 g) and methyl iodide (0.10 cc) in N,N-dimethylformamide (15 cc) is stirred for 24 hours. The mixture is diluted by adding isopropyl ether (30 cc). The supernatant liquors are decanted and the residue is stirred with ethyl ether (50 cc). The precipitate is filtered off and dried under reduced pressure (0.1 mm Hg; 0.013 kPa) at 20° C. This gives the syn isomer of 2-benzhydryloxycarbonyl-7-{2-[(2-t-butoxycarbonylprop-2-yl)-oxyimino]-2-(2-tritylaminothiazol-4-yl)-acetamido} -3-[2-(1-methyl-3-pyridinio-amino)-thiazol-5-yl]-8-oxo-5-thia-1-azabicyclo[4.2.0]oct-2-ene 5-oxide iodide (1.53 g).

Infra-red spectrum (CHBr$_3$), characteristics bands (cm$^{-1}$): 3380, 3100, 2500, 1806, 1730, 1675, 1600, 1505, 1450, 1370, 1145, 755, 700, 675.

Proton NMR spectrum (250 MHz, DMSO-d$_6$, δ in ppm, J in Hz): 1.36 (s, 9H, —c(CH$_3$)$_3$); 1.44 and 1.45 (2s, 6H, >C(CH$_3$)$_2$); 3.83 and 4.37 (2d, J=18.5, 2H, —SCH$_2$—);

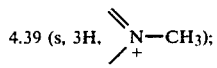

4.39 (s, 3H, ⟩N$^+$—CH$_3$);

5.12 (d, J=5, 1H, —H in the 6-position); 6.08 (dd, J=9 and 5, 1H, —H in the 7-position); 6.80 (s, 1H, —H in the 5-position of the thiazole); 6.95 (s, 1H, —COO—CH(C$_6$H$_5$)$_2$); 7 to 7.4 (mt, aromatic protons and —H in the 4-position of the thiazole); 8.05 (dd, J=8 and 6, 1H, —H in the 5-position of the pyridinio); 8.35 (d, J=9, 1H, —CO—NH—); 8.41 (d broad, J=8, 1H in the 4-position of the pyridinio); 8.6 (d, J=6, 1H, —H in the 6-position of the pyridinio); 8.78 (s, 1H, —NHC(C$_6$H$_5$)$_3$); 9.19 (s broad, 1H, —H in the 2-position of the pyridinio); 11.33 (b, 1H, >NH).

Trifluoroacetic acid (6.5 cc) and distilled water (0.65 cc) are added to a solution, cooled to 5° C., of the syn isomer of 2-benzhydryloxycarbonyl-7-{2-[(2-t-butoxycarbonylprop-2-yl)-oxyimino]-2-(2-tritylaminothiazol-4-yl)-acetamido}-3-[2-(1-methyl-3-pyridinio-amino)-thiazol-5-yl]-8-oxo-5-thia-1-azabicyclo[4.2.0]oct-2-ene 5-oxide (1.25 g) in anisole (1 cc). The mixture is stirred for 10 minutes at this temperature and then for 1 hour 15 minutes at 22° C. The reaction mixture is subsequently diluted with acetone (4.3 cc) and then with ethyl ether (40 cc). It is stirred for 5 minutes and filtered and the precipitate is washed with ethyl ether (5×10 cc). This gives the syn isomer of 7-{2-(2-aminothiazol-4-yl)-2-[(2-carboxyprop-2-yl)-oxyimino]-acetamido}-2-carboxy-3-[2-(1-methyl-3-pyridinio -amino)-thiazol-5-yl]-8-oxo-5-thia-1-azabicyclo[4.2.0]oct-2-ene 5-oxide ditrifluoroacetate (0.78 g) in the form of a greenish-brown powder.

Infra-red spectrum (KBr), characteristic bands (cm$^{-1}$): 3700, 2200, 1790, 1675, 1635, 1525, 1510, 1200, 1145, 800, 720, 670.

Proton NMR spectrum (250 MHz, DMSO-d$_6$, δ in ppm, J in Hz): 1.51 and 1.52 (2s, 6H), >C(CH$_3$)$_2$); 3.8 and 4.41 (2d, J=18.5, 2H, —S—Ch$_2$—); 4.36 (s, 3H,

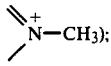

5.11 (d, J=5, 1H, —H in the 6-position); 6.08 (dd, J=8 and 5, 1H, —H in the 7-position); 6.86 (s, 1H, —H in the 5-position of the thiazole); 7.10 to 7.8 (b, 3H, —NH$_3$); 7.54 (s, 1H in the 4-position of the thiazole); 8.01 (dd, J=8.5 and 5, 1H, —H in the 5-position of the pyridinio); 8.44 (d broad, J=8.5, 1H, —H in the 4-position of the pyridinio); 8.56 (d, J=5, 1H, —H in the 6-position of the pyridinio); 8.63 (d, J=8, 1H, —CONH—); 9.35 (s broad, 1H, —H in the 2-position of the pyridinio); 11.6 (b, 1H,>N—H); 14 to 11 (b broadened, —COOH).

A solution of Amberlite LA-2 resin (1.75 cc) in methyl isobutyl ketone (5.35 cc) is added to a suspension of the syn isomer of 7-{2-(2-aminothiazol-4-yl)-2-[(2-carboxyprop-2-yl)-oxyimino]-acetamido}-2-carboxy-3-[2-(1-methyl-3-pyridinio-amino)-thiazo-5-yl]-8-oxo-5-thia-1-azabicyclo[4.2.0]oct-2-ene ditrifluoroacetate (0.71 g) in distilled water (21.3 cc). The mixture is stirred until the pH reaches 6.2, the liquid phase is then filtered and the filtrate is lyophilised. The lyophilisate is stirred for 2 hours in anhydrous ether (25 cc), filtered off, washed with ether (2×10 cc) and dried under reduced pressure (0.1 mm Hg; 0.013 kPa) to give the syn isomer of 7-{2-aminothiazol-4-yl)-2-[(2-carboxyprop-2-yl)-oxyimino]-acetamido}-2-carboxylato-3-[2-(1-methyl-3-pyridinioamino)-thiazol-5-yl]-8-oxo-5-thia-1-azabicyclo-[4.2.0] oct-2-ene 5-oxide (0.12 g) in the form of a yellow powder.

Infra-red spectrum (KBr), characteristic bands (cm$^{-1}$): 1780, 1670, 1610, 1530, 1395, 1040, 675.

Proton NMR spectrum (250 MHz, DMSO-d$_6$, δ in ppm, J in Hz): about 1.51 ppm (b, >C(CH$_3$)$_2$); 3.78 and 4.25 (2d, J=18.5, 2H, —S—CH$_2$—);

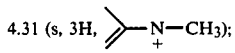

5.05 (d, J=4, 1H, —H in the 6-position); 5.9 (b, 1H, —H in the 7-position); 6.81 (s, 1H, —H in the 5-position of the thiazole); 7.23 (b, 2H, —NH$_2$); 7.49 (s, 1H, —H in the 4-position of the thiazole); 7.87 (b, 1H, —H in the 5-position of the pyridinio); 8.42 (b, 1H, —H in the 6-position of the pryidinio); 9.05 (b, 1H, H in the 4-position of the pyridinio); 5.20 (b, 1H, —H in the 2-position of the pyridinio).

REFERENCE EXAMPLE 3

The syn isomer of 2-benzhydryloxycarbonyl-7-[2--(2-t-butoxycarbonylprop-2-yl)-oxyimino-2-(2-tritylaminothiazol-4-yl)-acetamido]-3-[2-(1-methyl-3-pyridinio-amino)-thiazol-5-yl]-8-oxo-5-thia-1-azabicyclo[4.2.0]oct-2-ene 5-oxide iodide, obtained as in Reference Example 2, can be treated in the following manner:

N,N-dimethylacetamide (2.4 cc) and then phosphorus trichloride (1.06 cc) are added to a solution, cooled to 0° C., for the syn isomer of 2-benzhydryloxycarbonyl -7-[2-(2-t-butoxycarbonylprop-2-yl)-oxyimino]-2-(2-tritylaminothiazol-4-yl)-acetamido]-3-[2-(1-methyl-3-pyridinioamino)-thiazol-5-yl]-8-oxo-5-thia-1-azabicyclo[4.2.0]oct-2-ene 5-oxide iodide (3.76 g) in methylene chloride (30 cc). The reaction mixture is stirred for 45 minutes at 0° C. and then diluted with ethyl acetate (120 cc). A product precipitates and the precipitate is filtered off and washed with ethyl acetate (3×25 cc) and ethyl ether (2×25 cc). The product is dissolved in methylene chloride (100 cc) and then treated with 3S charcoal. The filtrate is concentrated to dryness under reduced pressure (100 mm Hg; 13.3 kPa) and the residue is taken up in ethyl ether (50 cc). The heterogeneous mixture is filtered and the solid is washed with ethyl ether (3×15 cc). It is dried under reduced pressure (0.1 mm Hg; 0.013 kPa) to give the syn isomer of 2-benzhydroyloxycarbonyl-7-[2-(2-t-butoxycarbonylprop-2-yl)-oxyimino-2-(2-tritylaminothiazol-4-yl)-acetamido]-3-[2-(1-methyl-3-pyridinio-amino)-thiazol-5-yl]-8-thia-1-aza bicyclo[4.2.0]oct-2-ene iodide (2.95 g).

Infra-red spectrum (KBr) characteristic bands (cm$^{-1}$): 2980, 2940, 1790, 1728, 1698, 1595, 1575, 1530, 1510, 1450, 1375, 1225, 1142, 1003, 760, 705.

Proton NMR spectrum (250 MHz, DMSO-d$_6$, δ in ppm, J in Hz): 1.38 (s, 9H, —COO—C(CH$_3$)$_3$); 1.42 (s, 6H, >C(CH$_3$)$_2$); 3.79 and 3.94 (2d, J=17.5, 2H, —S—CH$_2$—);

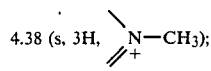

5.27 (d, J=5, 1H, —H in the 6-position); 5.85 (dd, J=8 and 5, 1H, —H in the 7-position); 6.72 (s, 1H, —H in the 5-position of the thiazole); 6.90 (s, 1H, —COO—CH(C$_6$H$_5$)$_2$); 6.95 to 7.4 (mt, aromatic protons+H in the 4-position of the thiazole); 8.05 (dd, J=8 and 5.5 1H, —H in the 5-position of the pyrioinio); 8.39 (d, J=8, 1H, —H in the 4-position of the pyridinio); 8.59 (d, J=5.5, 1H, —H in the 6-position of the pyridinio; 8.83 (s, 1H, —NH—C(C$_6$H$_5$)$_3$); 9.16 (s broad, 1H, —H in the 2-position of the pyridinio); 9.48 (d, J=8, 1H, —CO—NH—); 11.29 (b, 1H, —NH—).

A solution of the syn isomer of 2-benzhydryloxyc arbonyl-7-[2-(2-t-butoxycarbonylprop-2-yl)-oxyimino]-2-(2-tritylaminothiazol-4-yl)-acetamido]-3-[2-(1-methyl-3-pyridinio-amino)-thiazol-5-yl]-8-oxo-5-thia-1-azabicyclo[4.2.0]oct-2-ene iodide (2.85 g) in formic acid (42.8 cc) and anisole (4.3 cc) is heated at 50° C. for 30 minutes. The mixture is then diluted with distilled water (14.3 cc) and stirred at 50° C. for 15 minutes. The reaction solution is concentrated to dryness under reduced pressure (0.1 mm Hg; 0.013 kPa) at 40° C. The residue is taken up in ethanol (100 cc) which is evaporated off under reduced pressure (0.1 mm Hg; 0.013 kPa) to a residual volume of about 40 cc. The operation is repeated and the product is filtered off and washed with ethanol (2×25 cc), ethyl acetate (2×25 cc) and ethyl ether (2×25 cc). The product (0.95 g) is dried under reduced pressure (0.1 mm Hg; 0.013 kPa). A portion of this (0.58 g) is taken and dissolved in anisole (0.75 cc). This gives a brown solution, which is cooled to about 5° C. A cold solution of trifluoroacetic acid (4.90 cc) and distilled water (0.49 cc) is added. The mixture is stirred for 15 minutes at 5° C. and then for 1 hour 15 minutes at 25° C. The reaction mixture is diluted with acetone (3.2 cc), and ethyl ether (13 cc) is then run in. The mixture is stirred for 10 minutes and filtered and the precipitate is washed with ethyl ether (2×10 cc) and dried under reduced presssure (0.1 mm Hg; 0.013 kPa). This gives the syn isomer of 7-}2-(2-aminothiazol-4-yl)-2-[(2-carboxyprop-2-yl)-oxyimino]-acetamido}-2-carboxy-3-[2-(1-methyl-3-pyridinio-amino)-thiazol-5-yl]-8-oxo-5-thia-1-azabicyclo[4.2.0]oct-2-ene ditrifluoroacetate (0.60 g) in the form of a light brown powder.

Amberlite IR 45 resin (OH) (12 cc) is added to the syn isomer of 7-{2-(2-aminothiazol-4-yl)-2-[(2-carboxyprop-2-yl) oxyimino]-acetamido}-2-carboxy-3-[2-(1-methyl-3-pyridinio-amino)-thiazol-5-yl]-8-oxo-5-thia-1-azabicyclo[4.2.0]oct -2-ene ditrifluoroacetate (0.62 g) in distilled water (62 cc). The mixture is stirred for 40 minutes, the resin is filtered off and the filtrate is extracted with ethyl acetate (25 cc). The aqueous phase is concentrated on a rotary evaporator under reduced pressure (30 mm Hg; 4 kPa) to a residual volume of 50 cc. It is then lyophilised to give a pale yellow lyophilisate of the syn isomer of 7-{2-(2-aminothiazol-4-yl)-2-[(2-carboxyprop-2-yl)-oxyimino]-acetamido}-2-carboxylato-3-[2-(1-methyl-3-pyridinio-amino)-thiazol-5-yl]-8-oxo-5-thia-1-azabicyclo[4.2.0]oct-2-ene (0.15 g).

Infra-red spectrum (KBr), characteristic bands (cm$^{-1}$): 3420, 3100, 2985, 1765, 1670, 1600, 1575, 1525, 1470, 1390, 1360, 1335, 1290, 1220, 1150, 1075, 1030, 980, 910, 830, 810, 765, 670, 610, 570, 530, 430, 375.

Proton NMR spectrum (250 MHz, DMSO-d$_6$, δ in ppm, J in Hz); 1.47 and 1.50 (2s, 6H, >C(CH3)2); 3.75 and 3.90 (2d, J=17.5, 2H, —S—CH$_2$—);

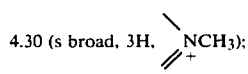

4.30 (s broad, 3H, NCH₃);

5.23 (d, J=4, 1H, —H in the 6-position); 5.78 (dd, J=4 and 8, 1H, —H in the 7-position); 6.76 (s, 1H, —H in the 5-position of the thiazole); 7.26 (s broad, 2H, —NH$_2$); 7.50 (s, 1H, —H in the 5-position of the thiazole); 7.83 (b, 1H, in the 5-position of the pyridinio); 8.35 (d, 1H, H in the 6-position of the pyridinio); 9.02 (d, 1H, H in the 4-position of the pyridinio); 9.17 (s broad, 1H, —H in the 2-position of the pyridinio).

We claim:

1. A cephalosporin compound of the formula:

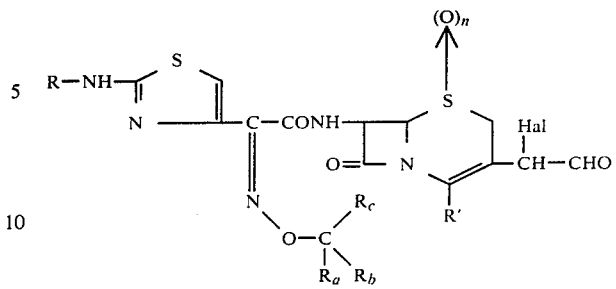

in which R represents an amino-protecting radical, R' represents a protected carboxyl radical, Hal represents a chlorine, bromine or iodine atom, and either R$_a$, R$_b$ and R$_c$ each represent a hydrogen atom, or R$_a$ represents a protected carboxyl radical and R$_b$ and R$_c$, which are identical or different, represents hydrogen atoms or alkyl radicals having 1 to 4 carbon atoms, or together form an alkylene radical having 2 to 5 carbon atoms, and n is equal to 0 or 1, the group —OCR$_a$R$_b$R$_c$ being in the syn position; and, when R$_b$ and R$_c$ are different, diastereoisomers of the said cephalosporin compound.

2. A cephalosporin compound according to claim 1, in which the amino-protecting radical R is selected from t-butoxycarbonyl, 2,2,2-trichloroethoxycarbonyl, trityl, benzyl, benzyloxycarbonyl, formyl, trifluoroacetyl, p-nitrobenzyloxycarbonyl, p-methoxybenzyloxycarbonyl or diphenylphosphinoyl groups or a radical defined by the formula:

in which Z is alkyl of 1 to 4 carbon atoms or 2,2,2-trichloroethyl, or phenyl or benzyl, these last two being unsubstituted or substituted by halogen, alkyl, alkoxy or nitro, or the symbols Z together form an alkylene radical of 2 or 3 carbon atoms.

3. A cephalosporin compound according to claim 1, wherein the carboxyl protecting radical in R' or R$_a$ is selected from t-butyl, 2,2,2-trichloroethyl, benzyhydryl, p-nitrobenzyl and p-methoxybenzyl.

4. A cephalosporin compound according to claim 1, in which the symbol R is a trityl radical, the symbol R' is a benzyhydryloxycarbonyl radical, the symbol Hal is a bromine atom and the symbols R$_a$, R$_b$ and R$_c$ each represent a hydrogen atom, or alternatively R$_a$ represents a t-butoxycarbonyl radical and R$_b$ and R$_c$ represent alkyl radicals, and, when R$_b$ and R$_c$ are different, diastereoisomers of the said cephalosporin compound.

5. A compound according to claim 1, which is the syn isomer of 2-benzhydryloxycarbonyl-3-(1-bromo-2-oxoethyl)-7-[2-methoxyimino-2-(2-tritylaminothiazol-4-yl)-acetamido]-8-oxo-5-thia-1-azabicyclo [4.2.0]oct-2-ene.

6. A compound according to claim 1, which is the syn isomer of 2-benzhydryloxycarbonyl-3-(1-bromo-2-oxoethyl)-7-[2-(2-t-butoxycarbonylprop-2-yl-oxyimino)-2-(2-tritylaminothiazol-4-yl)-acetamido]-8-oxo-5-thia-1-azabicyclo[4.2.0]-oct-2-ene.

* * * * *